US008169612B2

(12) United States Patent
Gao

(10) Patent No.: US 8,169,612 B2
(45) Date of Patent: May 1, 2012

(54) SYSTEM AND METHOD FOR PERFORMING ELLIPSOMETRIC MEASUREMENTS ON AN ARBITRARILY LARGE OR CONTINUOUSLY MOVING SAMPLE

(75) Inventor: Chao Gao, Fremont, CA (US)

(73) Assignee: KooSur Technologies Inc., Fremont, CA (US)

( * ) Notice: Subject to any disclaimer, the term of this patent is extended or adjusted under 35 U.S.C. 154(b) by 358 days.

(21) Appl. No.: 12/474,104

(22) Filed: May 28, 2009

(65) Prior Publication Data

US 2010/0302541 A1 Dec. 2, 2010

(51) Int. Cl.
G01J 4/00 (2006.01)
(52) U.S. Cl. .......... 356/369; 356/73; 356/614; 356/302; 356/492; 702/76; 702/85
(58) Field of Classification Search .............. 356/73, 356/369, 614, 507, 492, 331, 302, 623; 702/76, 702/85
See application file for complete search history.

(56) References Cited

U.S. PATENT DOCUMENTS 7,548,317 B2 * 6/2009 Sieck et al. ............ 356/445

* cited by examiner

Primary Examiner — Gregory J Toatley
Assistant Examiner — Iyabo S Alli
(74) Attorney, Agent, or Firm — Stattler-Suh PC

(57) ABSTRACT

A method for calibrating an apparatus for ellipsometric measurements performed on an arbitrarily large or continuously moving sample, using a visible sample reference frame, and one or more laser sources in order to calibrate the ellipsometer for variations in the distance between the ellipsometer apparatus and the sample of interest. Included are techniques for projecting a first laser beam spot from an incident laser source onto a sample, then analyzing the position of the first laser beam spot relative to the center of the sample reference frame using human-aided measurements and confirmations and/or computer vision techniques. Then adjusting pivot points and/or apparatus-to-sample distance to achieve a first beam spot being located about the center of the sample reference frame, and concurrently intersecting the plane of the sample. Other techniques include changing the incidence and reflectance angle using a semi-circular track arc design with a stepping motor activating each goniometer arm.

18 Claims, 11 Drawing Sheets

SYSTEM AND METHOD FOR PERFORMING ELLIPSOMETRIC MEASUREMENTS ON AN ARBITRARILY LARGE OR CONTINUOUSLY MOVING SAMPLE

FIELD OF THE INVENTION

The present invention is directed towards ellipsometry, particularly as it relates to ellipsometry measurements performed on coated fibers in the form of fabric or tows.

BACKGROUND OF THE INVENTION

Ellipsometry is a versatile and powerful optical technique for the investigation of the physical properties of materials (e.g. a complex refractive index or dielectric function), including properties of thin films. Ellipsometry techniques can yield extremely accurate measurements, and certain ellipsometric measurement techniques provide unequaled capabilities for thin film metrology.

In contrast to ellipsometry, other measurement techniques (e.g. scanning electron microscopy, auger electron spectroscopy, transmission electron microscopy, X-ray photoemission spectroscopy, etc), while quite accurate, tend to require long set-up times, involved sample preparation, challenging (e.g. vacuum) environmental conditions, and are destructive to the sample. Spectroscopic Ellipsometry (SE), either variable wavelength or variable incidence angle, or both, however, is an optical technique, uses relatively low energy light sources, can be performed without physical contact with a sample, and accordingly is non-destructive in its application.

In general terms, an ellipsometer analysis changes in polarization of a probing light that is reflected off a sample. Ellipsometry can yield measurements pertaining to layers that are much thinner than the wavelength of the probing light itself, and ellipsometry can yield measurements that can then be used to calculate the complex refractive index of a thin film of material. In many practical applications (e.g. characterization of thin films, characterization of multi-layer semiconductor structures, etc), spectroscopic ellipsometry is commonly used to characterize film thickness for single layers or even the thicknesses of complex multilayer stacks ranging from a few angstroms or tenths of a nanometer to several micrometers.

In cases using a conventional ellipsometer, a sample containing the layers to be measured (e.g. a thin-film coated component, a silicon die, etc) is mounted in a location stationary to the ellipsometer apparatus, usually on a stage that is mechanically mounted to the ellipsometer apparatus. Thus movements of the apparatus also move the sample. However, for larger samples (e.g. sheets, rolls of fabric) it may be impractical or impossible to mechanically mount the ellipsometer apparatus to the sheet or fabric, or roll of material, or other large sample. Thus the sample-to-ellipsometer apparatus juxtaposition must be included in measurements. Moreover, measurements taken across the surface of the sheet or roll might each require calibration of the fabric-to-apparatus juxtaposition. In addition, conventional ellipsometers often require the sample to be mechanically mounted into the ellipsometer apparatus (e.g. the sample mounted onto a stage which is in turn affixed to the measurement system). In this configuration, existing ellipsometers have a fixed rotational axis for changing incidence and reflectance angle. For large samples, such as a 1 meter wide by 10 meter long sample of fabric, or, for continuously running samples such as a fiber tow, the measurement system has to be physically separated from the sample. Thus, new techniques are needed.

Other automated features and advantages of the present invention will be apparent from the accompanying drawings, and from the detailed description that follows below.

SUMMARY OF THE INVENTION

A method for calibrating an apparatus for ellipsometric measurements performed on an arbitrarily large sample, using a visible sample reference frame, and one or more laser sources in order to calibrate the ellipsometer for variations in the distance between the ellipsometer apparatus and the sample of interest. Included are techniques for projecting a first laser beam spot from an incident laser source onto a sample, then analyzing the position of said first laser beam spot relative to the center of the sample reference frame using human-aided measurements and confirmations and/or computer vision techniques. Then adjusting pivot points and/or goniometer arm arcs to achieve a first beam spot being located about the center of the sample reference frame, and each goniometer arm at the same angle relative to the sample. Other techniques include projecting a second laser beam spot onto a sample, and analyzing the beam spots relative to a centerpoint.

A method for changing incidence and reflectance angle for ellipsometers used for large or continuously running samples is disclosed. Included are techniques for changing the incidence and reflectance angle over range using a semi-circular track as an arc guide, so that the measuring system and the sample may remain separated while measurements are performed on the large or continuously moving sample.

An apparatus for performing ellipsometric measurements on an arbitrarily large sample, using a visible sample reference frame, the apparatus comprising a semi-circular track; a first laser source pivotally mounted to a first stage and mechanically coupled to said semi-circular track; a second laser source wherein said second laser source projects a laser beam within the sample reference frame; and a detector, pivotally mounted to a second stage, said second stage mechanically coupled to said semi-circular track, wherein the detector is movable to receive laser light reflected off the sample. The aforementioned apparatus elements are structurally connected such that the first stage and the second stage move in tandem so a radial movement of the first stage through an arc along the semi-circular track is equal and opposite to a radial movement of the second stage through an arc along the semi-circular track.

BRIEF DESCRIPTION OF THE DRAWINGS

A brief description of the drawings follows.

DETAILED DESCRIPTION

In the following description, numerous details are set forth for purpose of explanation. However, one of ordinary skill in the art will realize that the invention may be practiced without the use of these specific details. In other instances, well-known structures and devices are shown in block diagram form in order to not obscure the description of the invention with unnecessary detail.

As indicated, there is a need for techniques to calibrate ellipsometric apparatus when large samples (e.g. sheets of material, rolls of fabric, etc) are involved. Using one or more of the herein-described techniques may result in a range of such desired characteristics. Some of the desired characteristics are introduced in the following paragraphs.

Section 1. Overview

The embodiments herein generally relate to ellipsometric measurements taken on fibers, which fibers are coated with one or more layers of thin film—the properties of the film being the properties of interest. In some cases fibers are woven or otherwise organized into a fabric, and a width of fabric might be formed into a sheet, or strip, and/or rolled into a bolt of material.

Ellipsometric measurements can be taken from a fiber or other non-planar sample using a polarization and phase modulation ellipsometer (PPME). The resulting measurements can be used to gather or calculate the film thickness, refractive index, and extinction coefficient of the coating(s) and refractive index, and extinction coefficient of the substrate. These parameters in turn can be used to calculate or infer chemical composition, morphology, electrical conductivity and other properties. Uniformity or at least variance within some tolerance can be considered as a quality metric, thus PPME can be used in a quality assurance step in a manufacturing process or as a process control tool for fiber coating.

Fast Setup, Calibration, and Ellipsometric Sampling Time

Figure 1:
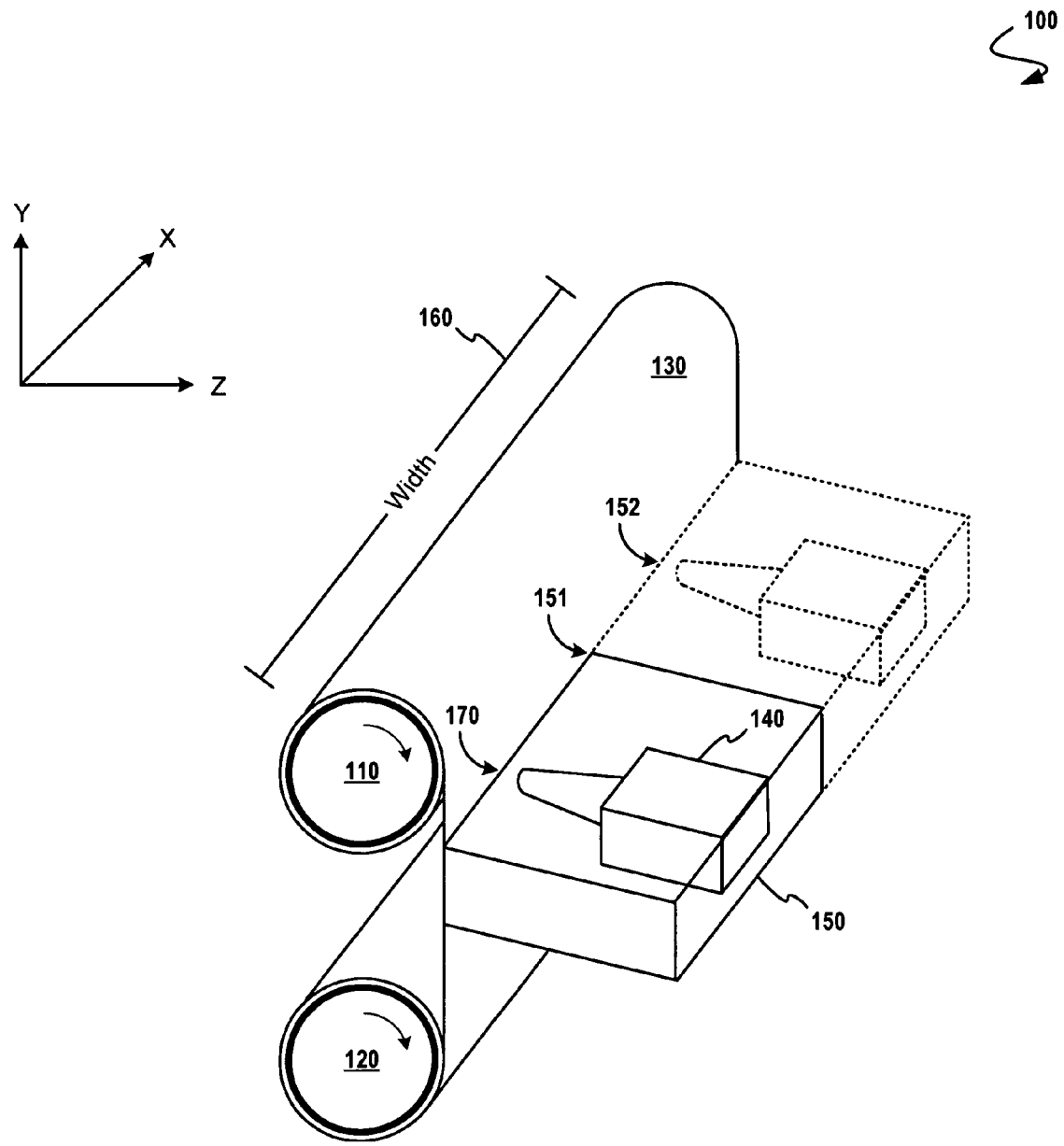
FIG. 1 shows a positioning system including an ellipsometer, according to one embodiment.

Inasmuch as large samples such as a fabric sheet can be rolled onto a bolt, and re-rolled onto a take-up bolt, it is reasonable and envisioned that the a PPME can be brought into the general proximity of the take-up apparatus. FIG. 1 shows a positioning system including an ellipsometer, according to one embodiment. As shown in FIG. 1, a bolt 110 is juxtaposed next to a take-up reel 120 so as to expose a surface of the fabric 130. One or more PPMEs 140 might be mounted within a housing 150. In some embodiments, a PPME 140 mounted within a housing 150 might also be mounted to a movable stage (not shown), also within a housing 150. Further, such a stage might be mechanically configured to permit positional adjustments on X, Y and Z axes, and such adjustment might be carried out under computer control.

Given such a configuration as shown in FIG. 1, measurements might be taken by the PPME along the width 160 of the bolt at point 170, point 151, point 152, or any other point on the accessible surface of the fabric. In fact a motorized stage and a corresponding control unit might be configured to traverse along width 160, taking ellipsometric measurements of the fabric periodically across the width. The bolt 110 can then be advanced a few degrees or a fraction of a degree, thus advancing the fabric to a new Y location, and ready for another set of ellipsometric measurements. Using a motorized stage and a sufficiently fast data collection apparatus, literally thousands of measurements can be taken across the surface area of a bolt of fabric within a very short time.

Automatic Ellipsometric Sampling, Data Collection, and Data Display

Given the positioning system of FIG. 1, it is reasonable and envisioned that entire bolts of fabric can be subjected to measurements performed semi-automatically with computer-aided calibration and computer-aided displays of data and quality metric assessments. Even in the case of highly sophisticated data displays (e.g. 3D models, simulated 3D models) the raw data can be collected in real-time (i.e. while the fabric is advanced) and processed for subsequent display at an operator's election.

Ellipsometry Principles

Figure 2:
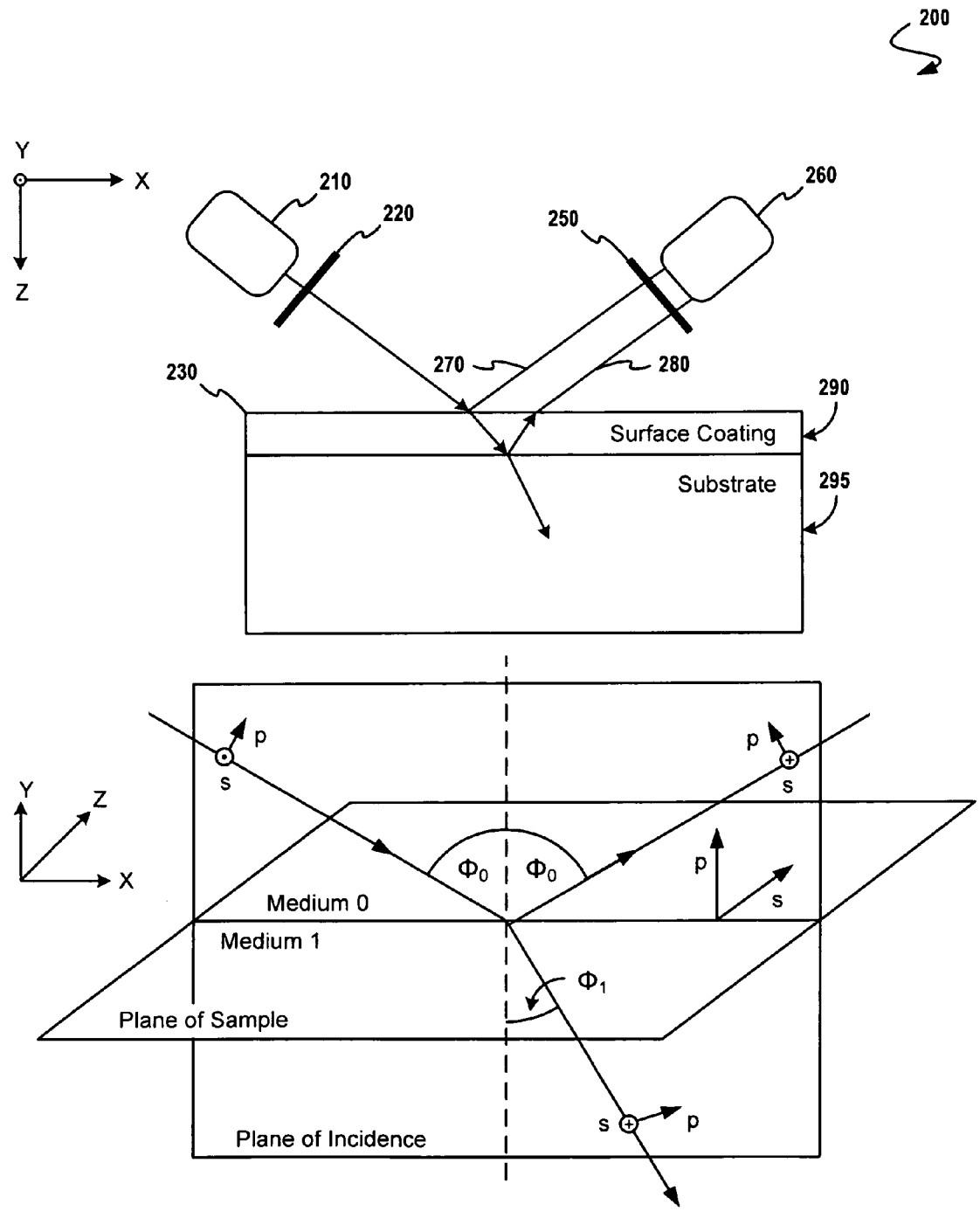
FIG. 2 is a schematic drawing showing the principles of ellipsometry, specifically showing angles of interest in ellipsometric analysis, according to one embodiment.

FIG. 2 is a schematic drawing showing the principle of ellipsometry, specifically showing angles of interest to ellipsometric analysis, according to one embodiment. As an option, the present system 200 of FIG. 2 may be implemented in the context of the architecture and functionality of FIG. 1. As shown the ellipsometer consists of a laser 210 (for example, a 632.8 nm He—Ne laser), a polarizer 220, a sample 230, an optional compensator (not shown), an analyzer 250, and a detector 260. The laser light beam is directed to the sample, from which some laser light 270 is reflected off the surface coating 290 of the sample 230. In most situations, some laser light is reflected off the substrate 295 as well, resulting in laser light reflected at 280. Note that the distance from the laser through reflected ray 270 is different from the distance from the laser through reflected ray 280.

In order to take a measurement using a null ellipsometer, the angles of the polarizer and analyzer are varied until a minimal signal is detected, that is, where the light reflected by the sample is linearly polarized. In other words, in order to obtain linearly polarized light after reflection, the polarizer must provide an optical retardation between the two incoming polarizations that exactly compensates for the optical retardation caused by the polarization-dependent reflections at each dielectric interface. Since the amplitude of both polarizations is set to be equal, the ratio of the amplitudes after reflection equals the tangent of the angle of the analyzer with respect to the normal.

The calculation of the expected angles of the polarizer and analyzer corresponding to the reflection coefficients at each of the dielectric interfaces for each polarization is:

$$r_{01,s} = \frac{n_0\cos\phi_0 - n_1\cos\phi_1}{n_0\cos\phi_0 + n_1\cos\phi_1} \quad (1)$$

(E field is parallel to the interface)

$$r_{01,p} = \frac{n_0\cons\phi_1 - n_1\cons\phi_0}{n_0\cons\phi_1 + n_1\cons\phi_0} \quad (2)$$

(E field is parallel to the incidence place)

$$r_{12,s} = \frac{n_1\cos\phi_1 - n_2\cos\phi_2}{n_1\cos\phi_1 + n_2\cos\phi_2} \quad (3)$$

(E field is parallel to the interface)

$$r_{12,p} = \frac{n_1\cos\phi_2 - n_2\cos\phi_1}{n_1\cos\phi_2 - n_2\cos\phi_1} \quad (4)$$

Figure 3:
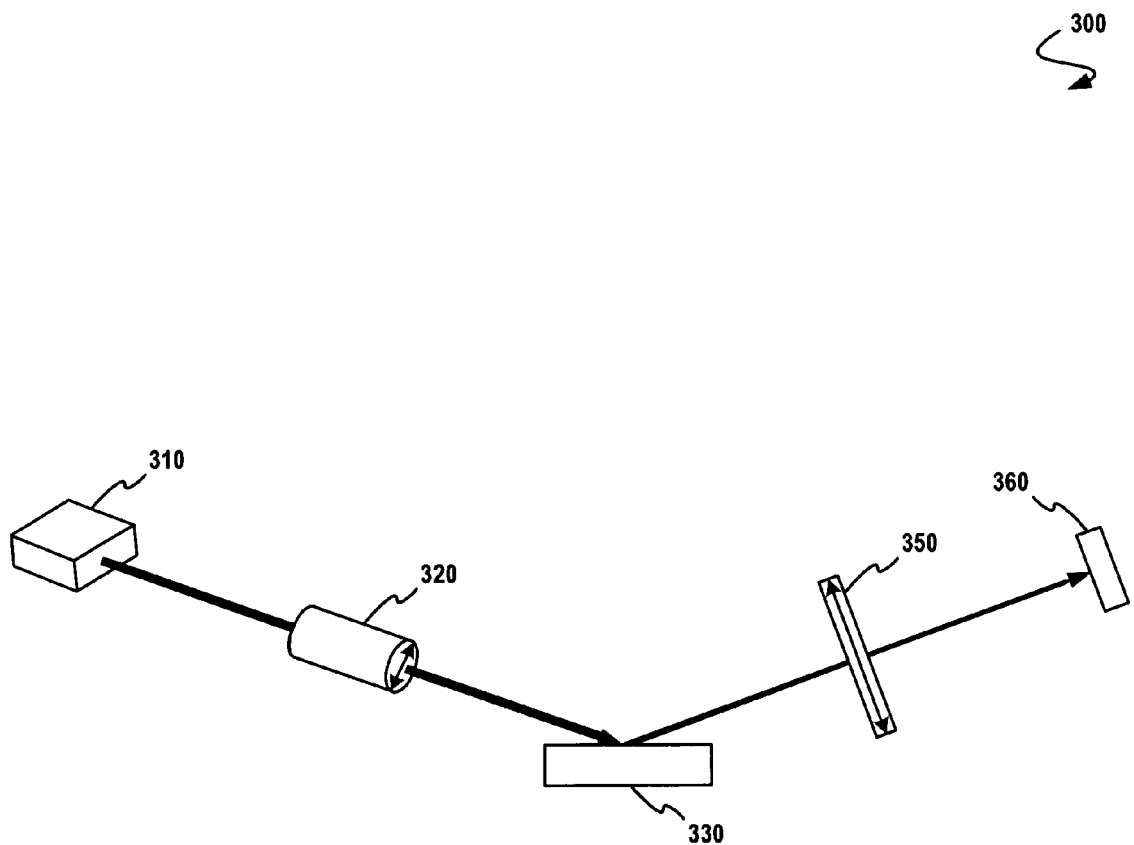
FIG. 3 shows an ellipsometer using a rotating polarizer, according to one embodiment.

(E field is parallel to the incidence plane)

with $$n_0 \sin\phi_0 = n_1 \sin\phi_1 = n_2 \sin\phi_2 \quad (5)$$

where the subscripts, 0, 1 and 2 refer to air, the thin film coating layer 290, and the substrate 230, respectively, and $\phi_0$ and $\phi_1$ are the angle of the incident and transmitted wave with respect to the normal of the interface as shown in FIG. 3.

Using the Fabry-Perot equations, a combined (stack) reflection coefficient considering the two dielectric interfaces yield (i.e. air to coating and coating to substrate) can be obtained by:

$$r_s = \frac{A_{R,s}}{A_{I,s}} = \frac{r_{01,s} + r_{12,s}e^{-i\delta}}{1 + r_{01,s}r_{12,s}e^{-i\delta}} \quad (6)$$

and $$r_p = \frac{A_{R,p}}{A_{I,p}} = \frac{r_{01,p} + r_{12,p}e^{-i\delta}}{1 + r_{01,p}r_{12,p}e^{-i\delta}} \quad (7)$$

with $$\delta = \frac{4\pi n_1 d_1 \cos\phi_1}{\lambda} \quad (8)$$

where $\lambda$ is the laser wavelength and $d_1$ is the thickness of the thin film coating 290. Combining the above equations yields the expression for $r_p$ and $r_s$, namely the reflection coefficient of the dielectric stack for p polarization (parallel) and s polarization (perpendicular). Based on the above discussion, the ratio of the two reflection coefficients can be split into an amplitude and a phase factor, thereby defining the ellipsometer parameters $\Psi$ and $\Delta$:

$$\rho = \frac{r_p}{r_s} = \tan\Psi e^{i\Delta} \quad (9)$$

For single layer film coating, the ellipsometric parameters can also be written as Stokes parameters, i.e.

$$\rho = \tan\Psi e^{i\Delta} = \frac{S_{21}^P}{S_{11}^P} \frac{S_{11}^S}{S_{21}^S} \quad (10)$$

In the example of FIG. 2, the linearly polarized case is considered; thus, the S-matrixes are defined as:

$$S^P = \begin{vmatrix} S_{11}^P & S_{12}^P \\ S_{21}^P & S_{22}^P \end{vmatrix} = \begin{vmatrix} 1 & r_{01}^P \\ r_{01}^P & 1 \end{vmatrix} \begin{vmatrix} e^{i\beta_1} & 0 \\ 0 & e^{-i\beta_1} \end{vmatrix} \begin{vmatrix} 1 & r_{12}^P \\ r_{12}^P & 1 \end{vmatrix} \quad (11)$$

$$= \begin{vmatrix} (e^{i\beta_1} + r_{01}^P r_{12}^P e^{-i\beta_1}) & (r_{01}^P e^{-i\beta_1} + r_{12}^P e^{i\beta_1}) \\ (r_{01}^P e^{i\beta_1} + r_{12}^P e^{-i\beta_1}) & (e^{-i\beta_1} + r_{01}^P r_{12}^P e^{i\beta_1}) \end{vmatrix}$$

$$S^S = \begin{vmatrix} S_{11}^S & S_{12}^S \\ S_{21}^S & S_{22}^S \end{vmatrix} = \begin{vmatrix} 1 & r_{01}^S \\ r_{01}^S & 1 \end{vmatrix} \begin{vmatrix} e^{i\beta_1} & 0 \\ 0 & e^{-i\beta_1} \end{vmatrix} \begin{vmatrix} 1 & r_{12}^S \\ r_{12}^S & 1 \end{vmatrix} \quad (12)$$

$$= \begin{vmatrix} (e^{i\beta_1} + r_{01}^S r_{12}^S e^{-i\beta_1}) & (r_{01}^S e^{-i\beta_1} + r_{12}^S e^{i\beta_1}) \\ (r_{01}^S e^{i\beta_1} + r_{12}^S e^{-i\beta_1}) & (e^{-i\beta_1} + r_{01}^S r_{12}^S e^{i\beta_1}) \end{vmatrix}$$

where $$r_{01}^P = \frac{n_0\cos\phi_1 - n_1\cos\phi_0}{n_0\cos\phi_1 + n_1\cos\phi_0} \quad r_{01}^S = \frac{n_0\cos\phi_0 - n_1\cos\phi_1}{n_0\cos\phi_0 + n_1\cos\phi_1} \quad (13)$$

$$r_{12}^P = \frac{n_1\cos\phi_2 - n_2\cos\phi_1}{n_1\cos\phi_2 + n_2\cos\phi_1} \quad r_{12}^S = \frac{n_1\cos\phi_1 - n_2\cos\phi_2}{n_1\cos\phi_1 + n_2\cos\phi_2} \quad (14)$$

$$n_0\sin\phi_0 = n_1\sin\phi_1 = n_2\sin\phi_2 \quad (15)$$

and $$\beta_1 = \frac{2\pi d_1}{\lambda} n_1\cos\phi_1 = \frac{2\pi d_1}{\lambda} \sqrt{n_1^2 - n_0^2\sin^2\phi_0} \quad (16)$$

Thus, for a single-layer film on a substrate, $$\rho = \frac{r_{01}^P + r_{12}^P e^{i2\beta_1}}{1 + r_{01}^P r_{12}^P e^{-i2\beta_1}} \times \frac{1 + r_{01}^S r_{12}^S e^{-i2\beta_1}}{r_{01}^S + r_{12}^S e^{-i2\beta_1}} = \tan\Psi e^{i\Delta} \quad (17)$$

As developed below, the above equations can be applied in the contexts of a rotating-polarizer ellipsometer and/or a rotating-compensator ellipsometer.

Rotating-Polarizer Ellipsometer: Configuration and Principles

FIG. 3 shows an ellipsometer using a rotating polarizer, according to one embodiment. As an option, the present system 300 of FIG. 3 may be implemented in the context of the architecture and functionality of FIG. 1 through FIG. 2. As shown, the rotating-polarizer configuration includes a light source 310, a rotating polarizer 320, a sample 330, an analyzer 350 and a detector 360. In this configuration, the angle of the analyzer 350 is fixed at 45 degrees while the polarizer 320 rotates (continuously or periodically) while taking measurements.

The rotating polarizer ellipsometer has the smallest number of optical components, but may suffer from errors due to the polarization sensitivity of the system. The electric field vectors $E_x$ and $E_y$ of the laser after it has passed through the analyzer are given by the following expression of Jones formalism:

$$\begin{pmatrix} E_x \\ E_y \end{pmatrix} = \begin{pmatrix} \cos(A-A_0) & -\sin(A-A_0) \\ \sin(A-A_0) & \cos(A-A_0) \end{pmatrix} \begin{pmatrix} 1 & 0 \\ 0 & 0 \end{pmatrix} \times \quad (30)$$

$$\begin{pmatrix} \cos(A-A_0) & \sin(A-A_0) \\ -\sin(A-A_0) & \cos(A-A_0) \end{pmatrix} \begin{pmatrix} r_p & 0 \\ 0 & r_s \end{pmatrix} \times$$

$$\begin{pmatrix} \cos(P-P_0) & -\sin(P-P_0) \\ \sin(P-P_0) & \cos(P-P_0) \end{pmatrix} \begin{pmatrix} E_0 \\ 0 \end{pmatrix}$$

where P and A are the azimuth angles of the transmission axis of the polarizer and analyzer, respectively, and $E_0$ is the electric field amplitude of an input laser. Looking against the beam direction from the respective encoder azimuth positions, the positive angles of P and A might be measured in a counterclockwise manner. These azimuth angles are calibrated to determine the correction that is needed to place their transmission axes into the same zero azimuth as defined by the plane of incidence. In other words, when their transmission axes are in the plane of incidence, the polarizer has the offset angle $P_0$ and the analyzer has the offset angle $A_0$. Therefore, with respect to the plane of incidence, $P-P_0$ is the true azimuth angle of the polarizer, and $A-A_0$ s the true azimuth angle of the analyzer.

The intensity $I_D$ of the light at the detector is proportional to the square of the electric field, namely $I_D$ is proportional to $E_x E_x^* + E_y E_y^*$. Thus, the intensity $I_D(P, A)$ at the detector as a function of the analyzer or polarizer angle can be calculated from equations (1) and (2) and is given by:

$$I_D(P) = I_0(A-A_0)[1 + \alpha \cos(2P-2P_0) + \beta \sin(2P-2P_0)] + I_m \quad (31)$$

where $I_0$ is the average intensity and $\alpha$ and $\beta$ are the normalized Fourier coefficients defined as:

$$I_0(A-A_0) = \eta |r_s|^2 [\tan^2\psi \cos^2(A-A_0) + \sin^2(A-A_0)] \quad (32)$$

and where $$\alpha = \frac{\tan^2\psi - \tan^2(A-A_o)}{\tan^2\psi + \tan^2(A-A_o)} \quad (33)$$

and where $$\beta = \frac{2\tan\psi \cos\Delta \tan(A-A_o)}{\tan^2\psi + \tan^2(A-A_o)} \quad (34)$$

where $\eta$ and $r_s$ are constants. In Eq. 31, $I_m$ is the random noise due to the background signal level of the detector. The noise level can be determined when a shutter is blocking the laser beam in front of the laser. For an error-free system in the rotating-polarizer configuration, the intensity flux of the light at the detector is a sinusoidal function with second-order Fourier coefficients for the polarizer's true azimuth angle $P-P_0$. Equation 31 shows this calculation. The rotating-polarizer configuration is relatively insensitive to the polarization state of the light beam incident upon the detector, however it requires that the laser to be un-polarized. We can therefore deduce $\psi$ and $\Delta$ from the inverted forms of Equations 5 and 6 as follows:

$$\psi = \tan^{-1}\left(\sqrt{\frac{1+\alpha}{1-\alpha}} |\tan(A-A_o)|\right) \quad 0 \leq \psi \leq 90° \quad (35)$$

and $$\Delta = \pm\cos^{-1}\left(\sqrt{\frac{\beta^2}{1-\alpha^2}}\right) \quad -180° < \Delta \leq 180° \quad (36)$$

The intensity flux at discrete, equally spaced points of the azimuth angle are sampled, by mechanical revolution of the polarizer to determine the normalized Fourier coefficients in Equation 31, Within each mechanical revolution of the polarizer, the output irradiance at the detector has the form:

$$I_D(A_i, P_j) = I_0(A_i)[1 + \alpha_1 \cos(2P_j) + \beta_1 \sin(2P_j)] \quad (37)$$

where $A_i$ and $P_j$ are the discrete positions of azimuth angle of the analyzer and polarizer, respectively. The normalized Fourier coefficients in Equation 31 are obtained by using the discrete Fourier transform of the measured intensities $I(A_i, P_j)$ at the analyzer azimuth angle as follows:

$$\alpha_1(A_i) = \frac{2\sum_{j=1}^{N} I(A_i, P_j)\cos(2P_j)}{\sum_{j=1}^{N} I(A_i, P_j)} \quad (38)$$

and $$\beta_1(A_i) = \frac{2\sum_{j=1}^{N} I(A_i, P_j)\sin(2P_j)}{\sum_{j=1}^{N} I(A_i, P_j)} \quad (39)$$

By following a calibration procedure, the angular offset $A_o$ can be determined, and the calibrated normalized Fourier coefficients obtained, by:

$$\alpha = \alpha_1 \cos(2A_0) + \beta_1 \sin(2A_0) \quad (40)$$

and $$\beta = -\alpha_1 \sin(2A_0) + \beta_1 \cos(2A_0) \quad (41)$$

Rotating-Compensator Ellipsometer: Configuration and Principles

Figure 4:
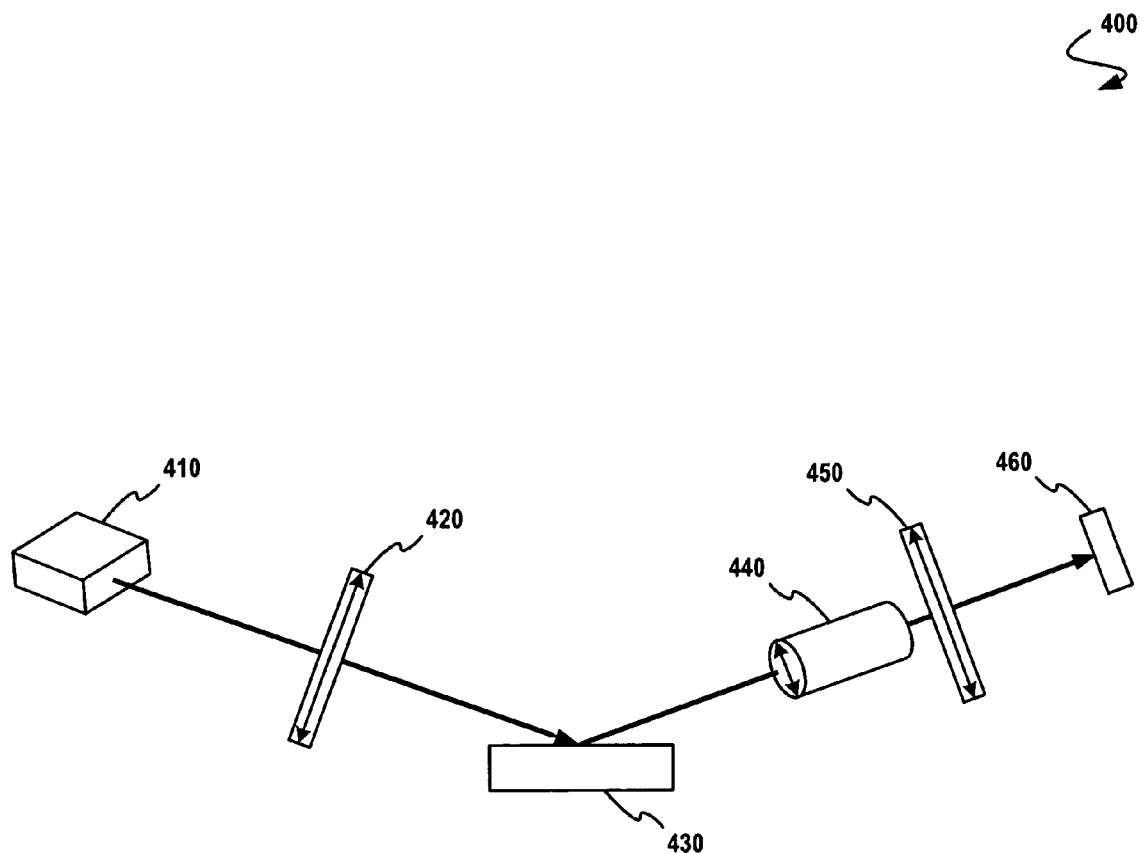
FIG. 4 shows an ellipsometer using a rotating compensator, according to one embodiment.

FIG. 4 shows an ellipsometer using a rotating compensator, according to one embodiment. As an option, the present system 400 of FIG. 4 may be implemented in the context of the architecture and functionality of FIG. 1 through FIG. 3. As shown, the rotating-compensator configuration includes a light source 410, a polarizer 420, a sample 430, a rotating compensator 440, an analyzer 450 and a detector 460. In this configuration, the angle of the polarizer 420 and analyzer 450 is fixed at 45 degrees, while the quarter wave compensator rotates (continuously or periodically) while taking measurements. The reflection intensity received by the detector is given by:

$$I_D = I_0(\alpha_0 + \alpha_2 \cos 2C + \beta_2 \sin 2C + \alpha_4 \cos 4C + \beta_4 \sin 4C) \quad (42)$$

where the Fourier coefficients $\alpha_0$, $\alpha_2$, $\beta_2$, $\alpha_4$, and $\beta_4$ are related to the Stokes parameters $[S_0, S_1, S_2, S_3]$ as:

$$\alpha_0 = \frac{1}{2}\left[s_0 + \frac{1}{2}(s_1\cos 2A + s_2\sin 2A)\right] \quad (43)$$

$$\alpha_2 = \frac{\sqrt{2}\,i}{4} s_3 \sin 2A$$

$$\beta_2 = -\frac{\sqrt{2}\,i}{4} s_3 \cos 2A$$

$$\alpha_4 = \frac{1}{4}(s_1 \cos 2A - s_2 \sin 2A)$$

$$\beta_4 = \frac{1}{4}(s_1 \sin 2A + s_2 \cos 2A)$$

Of course, inverting the equations yields the analytic expressions of the Stokes parameters as a function of the Fourier coefficients.

It can now be recognized that each measurement can yield two parameters. However, as shown in the following table, it is often desired to collect multiple parameters.

| Parameter | Layer | Symbol |
| --- | --- | --- |
| Coating thickness | 1 | $d_1$ |
| Refractive index | 1 | $n_1$ |
| Extinction coefficient | 1 | $k_1$ |
| Coating thickness | N | $d_n$ |
| Refractive index | N | $n_n$ |
| Extinction coefficient | N | $k_n$ |
| Refractive index | Substrate | $n_s$ |
| Extinction coefficient | Substrate | $k_s$ |

In general, for a sample with an N-layer coating on a substrate, the number of parameters to be extracted from the ellipsometer is 3N+2, which parameters can be measured in successive ellipsometric measurements.

Error Sources

Each of several ellipsometric techniques are subject to a variety of errors in measurements. Generally, the contribution to errors in an ellipsometric measurement can be understood by modeling the errors in the inputs to the mathematical formulas used to calculate the corresponding ellipsometric measurements.

Error types considered herein are:

Sampling Condition Errors. For example vibration, excessive airflow, ambient light leakage, etc.

Statistical Sampling Errors. For example, errors introduced by conditions present during sampling can often be averaged out by taking multiple measurements and/or by varying the configuration slightly for each measurement. For example, the wavelength of the laser might be varied slightly for each measurement, and an average or other statistical function applied to the group of measurements. In some embodiments multiple lasers might be used, at wavelengths $\lambda_1$, $\lambda_2$, $\lambda_3$, etc as a technique to vary the sampling configuration. In other embodiments, the angle of incidence might be varied. Regardless of the technique used for taking multiple samples, application of the mathematics using fixed precision values in calculations introduces statistical noise.

Intra-system Physical Alignment Errors. For example, errors introduced by physical alignment of the measurement instrumentation (i.e. independent of the location of the sample).

System-to-Sample Alignment Errors. For example, errors introduced by physical alignment of the measurement instrumentation relative to the location of the sample.

It is the system-to-sample aspect of alignment errors that are considered in the following sections.

Section 2. System-to-Sample Calibration Requirements

Figure 5:
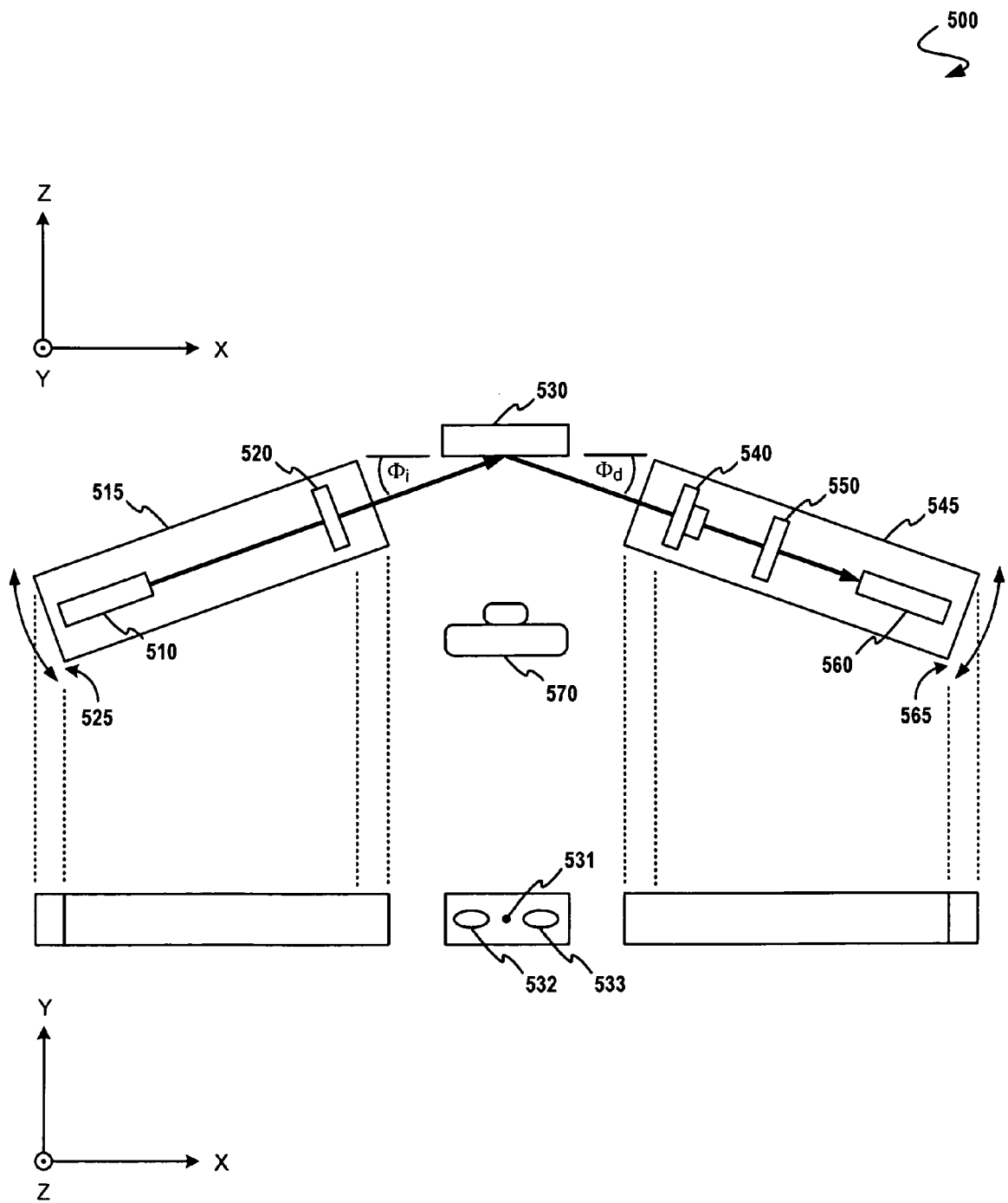
FIG. 5 is a schematic of a set-up using a rotating-compensator ellipsometer, including a goniometer design, for varying the positions of the incident optics stage so as to vary the angle of incidence, according to one embodiment.

FIG. 5 is a schematic of a setup involving a rotating-compensator ellipsometer, including a goniometer design, for varying the position of the incident optics stage so as to vary the angle of incidence $\Phi_i$, according to one embodiment. Similarly, the angle of the detector stage $\Phi_d$ can be varied so as to match the angle of incidence optics. As an option, the present system 500 of FIG. 5 may be implemented in the context of the architecture and functionality of FIG. 1 through FIG. 4. As shown, the rotating-compensator ellipsometer (system 500) includes a light source 510 (for example, a 632.8 nm He—Ne laser), a polarizer 520, a sample 530 (partial sample shown), an optional compensator 540, an analyzer 550, and a detector 560. Additionally, the rotating-compensator ellipsometer (system 500) includes a mounting stage (not shown) for the incident optics housing 515 and a mounting stage (not shown) for the incident optics housing 545.

Each housing 515 and 545 can be moved along an arc, 525 and 565, respectively, such that the angle of the centerline of the incidence optics mounting stage $\Phi_i$ equals the angle of the centerline of the detector mounting stage $\Phi_d$. In a calibrated configuration, that is, when the angle of the centerline of the incidence optics mounting stage $\Phi_i$ equals the angle of the centerline of the detector mounting stage $\Phi_d$, and when the camera 570 is focused on a frame of the sample, the laser beam from the incidence optics will project a spot centered on the sample.

While averaging or statistically combining multiple measurements tends to average out errors in sampling conditions, there remain many other contributors to measurement errors.

Also shown in FIG. 5 is a principal view of the rotating-compensator ellipsometer (system 500), showing the principal view projection of the XY plane, looking into the Z-axis. Of particular interest is the calibration of the laser beam spot on the sample. As shown in FIG. 5, the incident optics are mounted into a goniometer arm, adjustable such that the laser beam can present an elliptical spot with the ellipsis centered on the sample 530. As shown, the centerpoint of this spot is shown in the lower portion of FIG. 5 as point 531. Geometrically, even as the angle of the goniometer varies, the center of the ellipsis at point 531 remains the center through the range of the goniometer arm motion. However, under actual sampling conditions, the incident optics laser beam may not be perfectly centered around point 531. Such variations may be due to the physical design of the goniometer physical design, imperfections in optics, laser beam deviation, polarizer asymmetry, collimation errors, responses of the detector to polarization imperfections and many other factors that may vary from the ideal, theoretical design when realized in a real physical system. Inasmuch as in an un-calibrated system, the elliptical spot many not be centered precisely at point 531. A viewport (e.g. optical viewport, or camera and display) 570 is provided within the PPME ellipsometer system for use in calibration. Using such a viewport or other techniques discussed infra, the juxtaposition of any off-center laser beam (shown as ellipses 532 and 533) can be determined within some system-determined precision.

Especially in situations where the sample is not mounted in or on a mechanical fixture precisely located at 530, the laser spot might be incident on the sample at some point other than around point 531. Therefore, several techniques for controlling the distance between the ellipsometer mechanics and the sample are herein defined. Various embodiments of the invention employ sampling distance controls for taking accurate measurements of a large sample.

Figure 6:
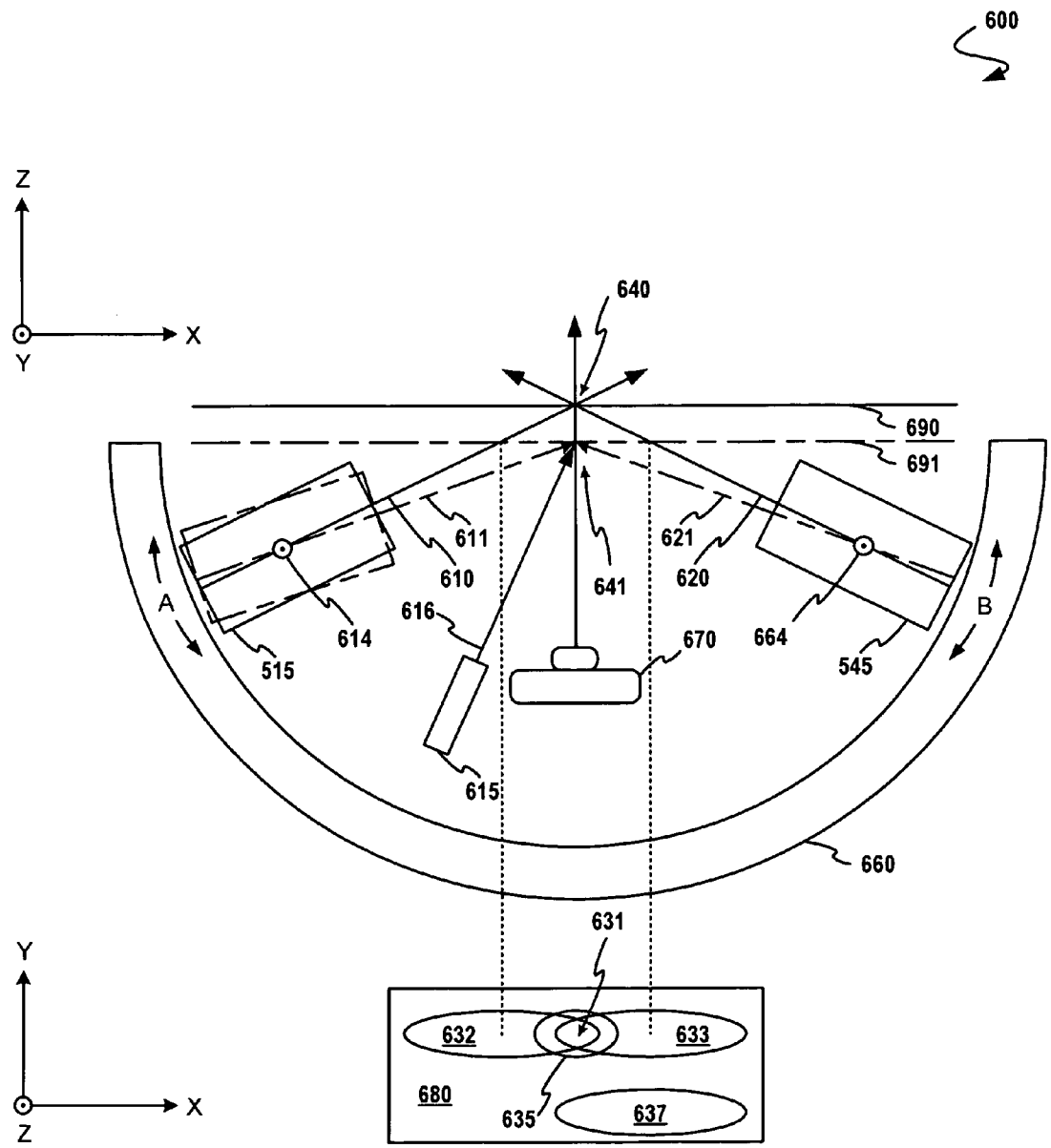
FIG. 6 shows a schematic representation of beam alignment calibration crossing, according to one embodiment.

FIG. 6 shows a schematic representation of beam alignment calibration crossing, according to one embodiment. As an option, the present system 600 of FIG. 6 may be implemented in the context of the architecture and functionality of FIG. 1 through FIG. 5. As shown, a laser beam 610 is directed toward a sample 690 at an angle of incidence $\Phi_i$, and a second beam 620 is directed toward the same sample 690 at an angle of incidence $\Phi_d$. As shown, the crossing of beam 610 and beam 620 occurs at plane 690, which is slightly behind (at 640) the plane of the surface of the sample to be measured 691. In this example, the camera 670 captures within frame 680 an image of the two beams, showing the unaligned ellipses, namely ellipse 632 formed by beam 610 and ellipse 633 formed by beam 620. That is, the center of elliptical beam pattern 632 is aligned slightly left of the theoretical centerpoint 631, and the center of elliptical beam pattern 633 is aligned slightly right of the theoretical centerpoint 631.

Also shown in FIG. 6 is the incident optics housing 515, which is mounted on a pivot point 614. Pivot point 614 is selected such that the housing 515 can be pivoted about point 614 via a stepping motor, or any other technique for controlling the angular orientation of housing 515 about the pivot point 614. Of course the pivot point 614 refers to the pivot point corresponding to the incidence optics. A second pivot point 664 corresponds to the detector optics, around which pivot point the detector housing 545 can be pivoted.

For confirming the position of the sample relative to the measurement instrument, a second, centering laser beam might be employed. This technique includes identification of the crossover point of the two laser sources, and further includes techniques for location of the sample fabric to be substantially in a plane that intersects the point of crossover. In some cases the two laser sources might be of visibly different wavelengths; for example the incident laser might be observable as a red laser beam, while the centering laser beam might be observable as a green laser beam. Referring to FIG. 6, to ease measurements and alignments, a centering laser source 615 might be employed to direct a beam 616 toward the sample. As shown in FIG. 6, this results in a crossover point between the incidence optics laser 611 and the centering laser at centerpoint 641. As shown, such a configuration would present a spot 635 within image frame 680, thus providing visible orientation of the ellipse 632 and ellipse 633 relative to spot 635. In some cases, the centering laser source 615 is mounted slightly off center relative to the camera 670, such that the camera housing does not occlude the centering laser beam. In other embodiments, the centering laser source is mounted slightly above the camera, or slightly below the camera. In another embodiment, the color of the laser sources might be selected from any of a group of colors providing color contrast with respect to any other laser beam. In still other embodiments, the centering laser source is centered such that the centering laser source beam travels a path parallel to the Z-axis and illuminates a spot centered at 641. In such a case, the camera may be mounted slightly off center to the left or right, or slightly off center above or below. In situations where the frame 680 results from a camera location slightly off center, various image processing techniques might be performed on the image within frame 680 to manipulate the perspective of the image to approximate the perspective of the image had the camera been perfectly centered.

Another alignment technique employs mounting a laser source to the mounting 545 that houses the detector, such that adjustments can be made to the spot location via adjustments at the pivot points 614 and 664, and such that the laser beams 611, 621 and 616 overlap at the plane of the sample 691, each sharing a common center, namely centerpoint 641. As is indicated via the beam pattern in the image frame 680, the incidence optics 515 should be rotated about pivot point 614 such than the beam ellipsis 632 is centered at point 641. A similar pivot adjustment can also be made to the detector optics housing 545 about pivot point 664.

In another embodiment, a laser source 620 might be included in the sample set-up and used in beam alignment calibration. Of course, such a laser source might be mounted on, or within, the housing 545 such that the laser beam is not occluded by the detector. As shown, the ellipse 637 is formed by a laser source mounted slightly below the detector.

As earlier indicated, errors introduced by the sample set-up can often be averaged out by taking multiple measurements and varying the sample configuration slightly for each measurement (for example, the angle of incidence might be varied). FIG. 6 depicts a goniometer design whereby the incidence optics housing 515 is mechanically affixed (not shown) to a semi-circular track 660 such that the housing 515 and its contents can traverse a range of degrees through arc A. Similarly, the detector optics housing 545 is mechanically affixed (not shown) to a semi-circular track 660 such that the housing 545 and its contents can traverse a range of degrees through arc B, noting that it is possible that one goniometer arm can be rotated independently of the other goniometer arm, or in tandem. As can now be understood, such design permits a physical separation of the sample from the measuring system (e.g. in the case of large or continuously moving samples) while the variations of incidence and reflectance angles can vary throughout the range required for accurate measurements.

Another technique employs a mechanical device capable of creating and maintaining a physical separation between the sample and the measurement instrument. Using such a technique for example, the XY plane of the sample 690 can be moved in the Z-axis to present an XY plane of the sample at 691; that is, such that the plane 691 intersects with point 640. One such design uses a mechanical device capable of creating and maintaining a physical separation between the sample and the measurement instrument in combination with pattern recognition techniques by comparing image size so as to determine the distance between the sample and the measurement instrument. Of course this technique may require calibration so that the focal length of the high-resolution camera 670 is adjusted such that a particular physical separation distance between the sample and the measurement instrument is calibrated prior to measurements, and then kept constant through multiple measurements. Of course this technique for gauging the physical separation between the sample and the measurement instrument may be used in combination with any of the aforementioned techniques (e.g. two laser or three laser systems), or it may be used alone. In some combinations, the physical distance between the sample and the measurement instrument can be roughly gauged using the mechanical device capable of creating a physical separation between the sample and the measurement instrument, and then finely tuned by making pivot adjustments at pivot points 614 and 664. The correct configuration is when the cross point of the two beams intersects the XY plane of the sample. This crossover at the plane of the sample can of course be observed by a person, or through use of pattern recognition algorithms applied to the image in the frame produced by the CCD camera 670.

Of course, as earlier mentioned, the calibration of other juxtapositions and parameters (e.g. affixing and alignment of housing 515 to semi-circular track 660, affixing and alignment of housing 545 to semi-circular track 660, etc) might be performed, and might be performed well in advance of the abovementioned beam alignment calibration.

In accordance with ellipsometer design of FIG. 6, an apparatus for performing ellipsometric measurements on an arbitrarily large sample, using a visible sample reference frame may be described. In one embodiment, the apparatus includes a semi-circular track 660. A first laser source, optionally positioned within a housing 515 is pivotally mounted to a movable incident optics stage, said movable incident optics stage mechanically coupled to said semi-circular track 660, wherein said first laser source projects a laser beam within the sample reference frame. Included in embodiments is a second laser source 615 wherein said second laser source projects a laser beam within the sample reference frame. A detector, optionally positioned within a housing 545, is pivotally mounted to a detector optics stage, said a detector optics stage mechanically coupled to said semi-circular track, wherein said detector is movable to receive laser light reflected off the sample. By virtue of the mechanical coupling between the incident optics stage and the semi-circular track 660 and corresponding mechanical coupling between the detector optics stage and the semi-circular track 660, the two stages may be moved in tandem such that a radial movement of one stage through an arc along the semi-circular track 660 is equal and opposite to a radial movement of the other stage through an arc along the semi-circular track. In some embodiments, changing the incidence and reflectance angle is accomplished by an arc design using a semi-circular track, whereby the two stages may be moved with two stepping motors, each stepping motor actuating a corresponding goniometer arm so the measuring system and the sample are separated while measurements are performed on the large or continually moving sample. Of course, the range of movement of the stages is subject to physical limitations. As shown, the range of movement of a stage along an arc is roughly one half of a circle.

Section 3. Computer-Assisted System-to-Sample Calibration Sequence

Figure 7:
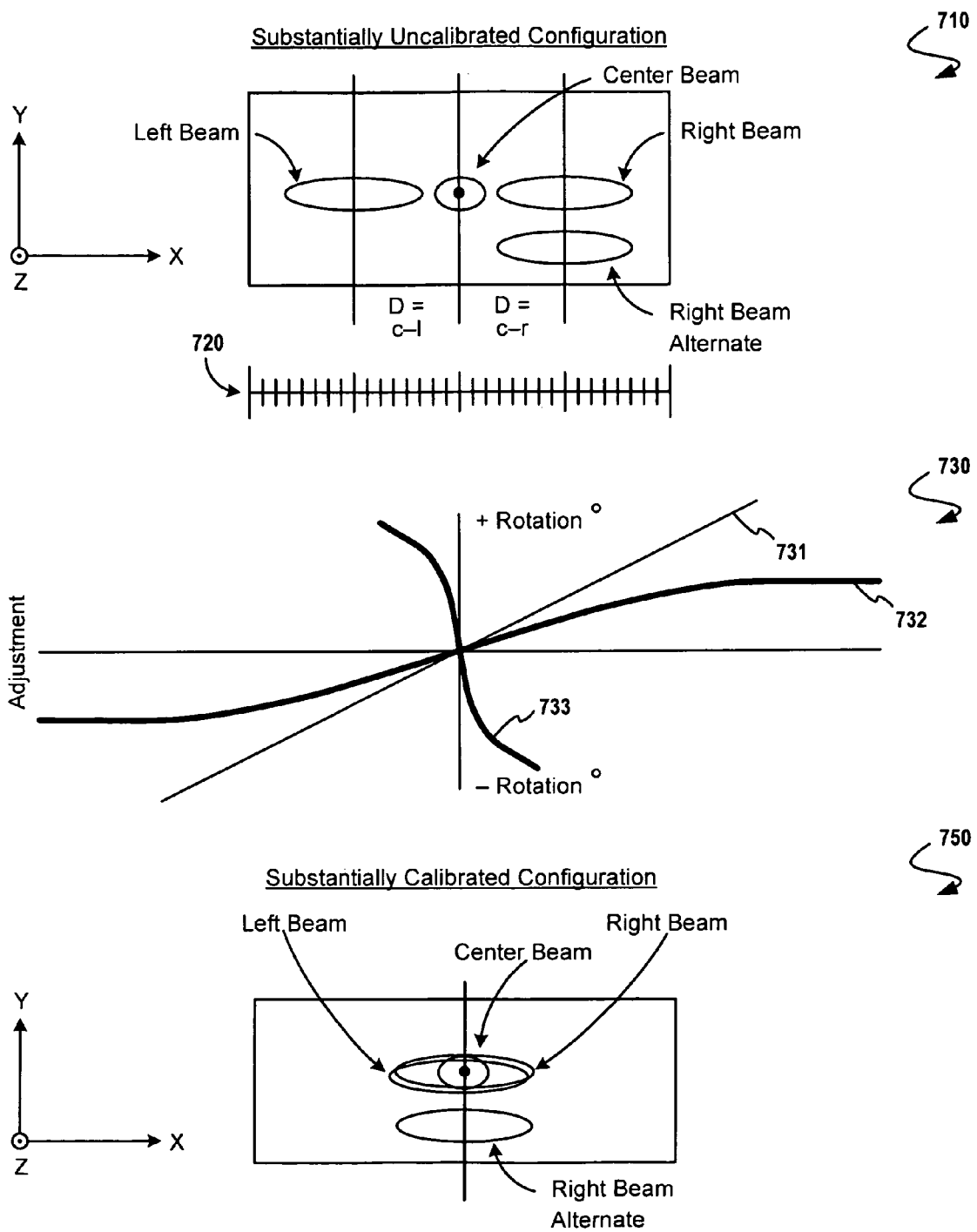
FIG. 7 depicts a calibration technique, including a calibration curve, used to translate a linear distance (e.g. the distance between the laser beam spot ellipse center to the true center of the frame as captured by the camera), according to one embodiment.

FIG. 7 depicts a calibration technique, including a calibration curve, used to translate a linear distance (e.g. the distance between the laser beam spot ellipse center to the true center of the frame as captured by the camera). As an option, the present systems 710, 730, 750 of FIG. 7 may be implemented in the context of the architecture and functionality of FIG. 1 through FIG. 6. As shown, the frame at 710 has multiple laser spots, including a left beam ellipse, a center beam ellipse (though the center beam ellipse is substantially circular), and a right beam ellipse. Each ellipse has a center, and each ellipse has a needed X-axis adjustment. The adjustment needed for the left beam is equal to $d_{adj\_x}=c_{frame\_x}-center_{left\_x}$. The adjustment needed for the right beam is equal to $d_{adj\_x}=c_{frame\_x}-center_{right\_x}$. The adjustment needed for the right alternate beam is equal to $d_{adj\_x}=c_{frame\_x}-center_{rightalternate\_x}$. The adjustment $d_{adj}$ might be accomplished by signaling a stepping motor to turn some number of degrees in a positive sense (e.g. clockwise) or a negative sense (e.g. counterclockwise). The function for calculating a correcting rotation from an adjustment distance might be represented as curves (e.g. 731, 732, 733) and the calculation might be implemented by a computer algorithm, or might be implemented using a computer-readable table of values for translating a value for $d_{adj}$ into a value for degrees of rotation. Of course a wide variety of shapes of transformation curves 731, 732, 733 might be appropriate inasmuch as any variety of mechanical features might be used to effect the adjustment, and such adjustment functions might not be linear, and in fact might not even be continuous functions.

Continuing, the stepping motor might in turn adjust a housing (e.g. 515, 545) around a pivot point 614 or 664, respectively. The stepping motor might in turn adjust the angle of a goniometer arm, or might adjust the distance between the ellipsometer system and the sample. After a correct adjustment (or possibly multiple correct adjustments), the beam spot ellipse is intended to be oriented quite similarly to the depiction at 750. It should be emphasized that there are many ways to calculate the distance $d_{adj}$. In one embodiment, a human operator views the pattern (e.g. on a computer display) in the frame as depicted at 710, and reading from a scale 720, enters the values for $d_{adj}$. In other embodiments, computer vision is used to identify the ellipses from an image 750, and extract adjustment measurement from the image using computer vision and or image processing techniques.

Figure 8:
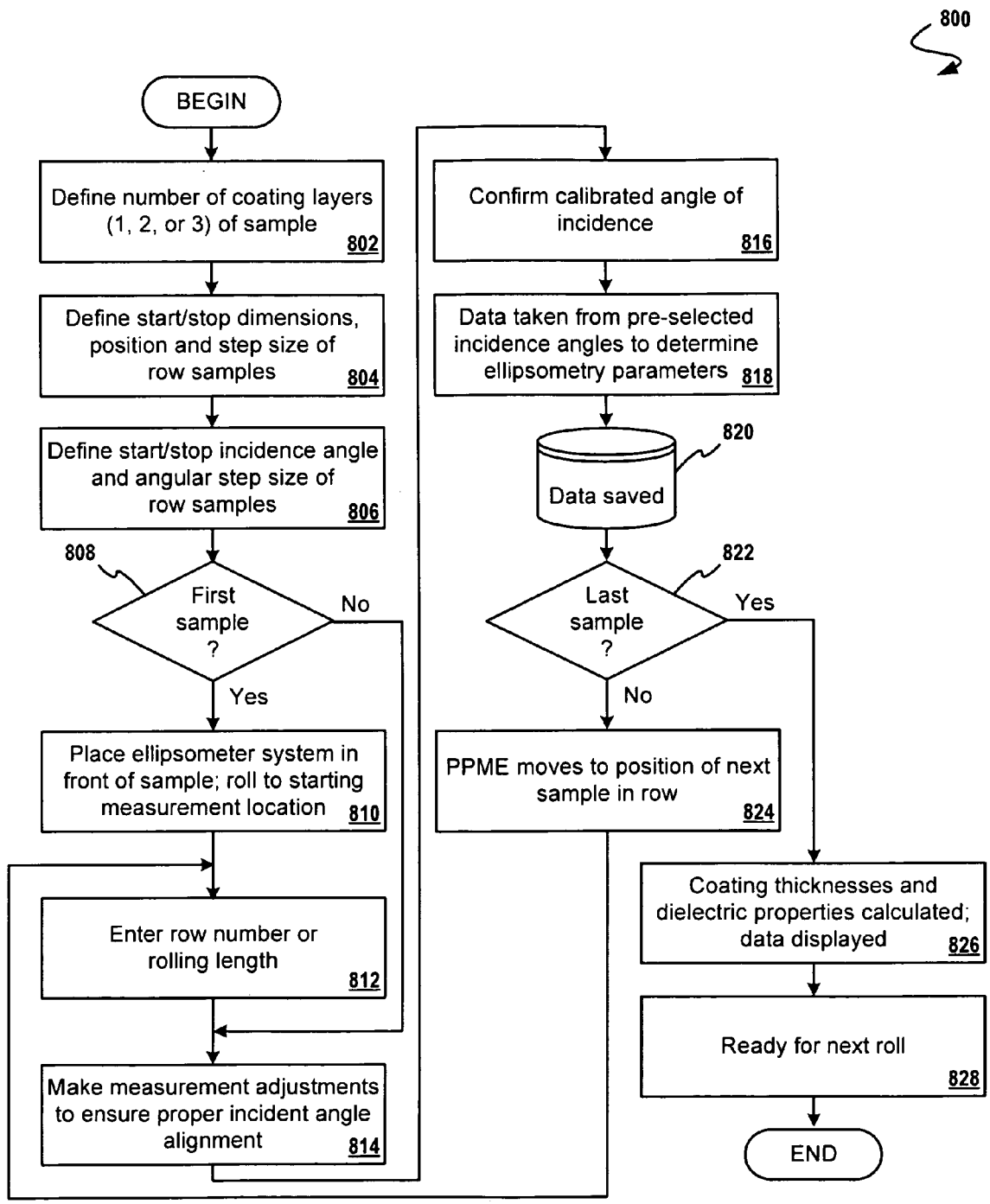
FIG. 8 is a flowchart of steps and decisions for performing ellipsometric measurements on an arbitrarily large or continuously moving sample, using a goniometer design, according to one embodiment.

FIG. 8 is a flowchart of steps and decisions for calibration of an apparatus for ellipsometric measurements performed on an arbitrarily large sample, using a goniometer design, according to one embodiment. As an option, the present system 800 may be implemented in the context of the architecture and functionality of FIG. 1 through FIG. 7. As shown, the system 800 includes steps for calibrating the instrument based on the type of sample, steps for taking a series of measurements, and steps for display of the series of measurements. In particular, the system 800 includes a step 802 for defining the number of coating layers. Of course, recall that the ellipsometric parameters for a single layer or multiple-layers on a substrate is given (in Stokes parameter form) as $$\rho = \tan\Psi e^{i\Delta} = \frac{S_{21}^P}{S_{11}^P}\frac{S_{11}^S}{S_{21}^S}.$$

Continuing, step 804 is for defining various sample size characteristics, and the organization of samples to be taken. For example, if the sample is a bolt of fabric, 1 meter wide by 25 meters in length, the samples might be organized as 25 rows of (for example) four samples per row, for a sample array totaling 100 points. As a more specific example, the sample fabric might be described as 1 meter in width and 25 meters in length and the start/stop position and step size of the sample might be described as 0.1 m/1.0 m and a sampling step size as 0.1 m; thus samples would be taken for each row at 0.1 m, 0.2 m, 0.3 m, 0.4 m, 0.5 m, 0.6 m, 0.7 m, 0.8 m, 0.9 m and 1.0 m.

Step 806 is for defining the start/stop range of the angle of incidence for each point. That is, as earlier indicated, the angle of incidence can be varied during a sampling session. Also, as earlier described, varying the angle permits collection of additional ellipsometric parameters. The number of (sample) stops in part depends on the number of layers of the sample, and in part depends on the desired statistical accuracy across a larger number of (sample) stops. As shown in FIG. 6, the angle of incidence can be varied through the range of the degrees traversed by the arc of one goniometer arm (e.g. left side, incidence optics) and/or the arc of the other goniometer arm (e.g. right side, detector optics). Step 806 can also be used for defining the angular step size of the sample as further discussed below.

Decision 808 occurs at the beginning of a loop section that provides for calibrating and collecting measurements at multiple points across the sample. That is, if this is the first measurement to be taken from a bolt of fabric, then the ellipsometer system must be positioned with respect to a large sample (see operation 810) and the roll parameter must be calibrated (see operation 812). Otherwise, if this is not the first measurement to be taken from a bolt of fabric, then proceed to step 814, thus continuing with the measurement adjustments to ensure proper incident angle alignment.

Step 816 serves for confirming computer-aided measurements of the angle of incidence settings of the stages corresponding to housing 515, and housing 545 at the goniometer arm(s). That is, if there is a visibly detectable misalignment of the ellipsometer system as compared to the sample, that misalignment is corrected. The image captured by the camera is analyzed (via computer image analysis or human analysis), resulting in a small adjustment at the pivot points, and/or of the goniometer arm(s). When the small goniometer arm adjustments are made and beam incidence angles are confirmed; the goniometers are calibrated.

Step 818 then proceeds. In an automated fashion, under computer control, multiple measurements are taken at that location on the fabric. More specifically, the number and characteristics of the multiple measurements taken depend on the initialization steps 802, 804, and 806. For example, the start/stop position and step size might have been described as 51°/69° and the angular step size described as 2°, thus resulting in measurements taken at 51°, 53°, 55°, 57°, 59°, 61°, 63°, 65°, 67°, and 69°, and at step 818 such measurements might be taken in some sequence. Results are saved to a storage media for later retrieval (see operation 820).

If the point just sampled in step 810 was not the last point (see decision 822) intended to be sampled across the fabric dimensions (as can be determined by the parameters entered in step 804), then the PPME is moved to the position of the next sample in the row (see step 824) and the sequence beginning at step 812 is repeated. If the point just sampled in step 810 was the last point (see decision 822) intended to be sampled across the fabric dimensions (as can be determined by the parameters entered in step 804), then the aggregated measurements can be displayed, possibly including one or more graphs showing coating thicknesses, refraction indexes, extinction coefficients for each layer and, optionally, the refraction index and extinction coefficient for the substrate (see step 826). At step, 828 the ellipsometer system is ready for use on a new fabric sample.

Figure 9:
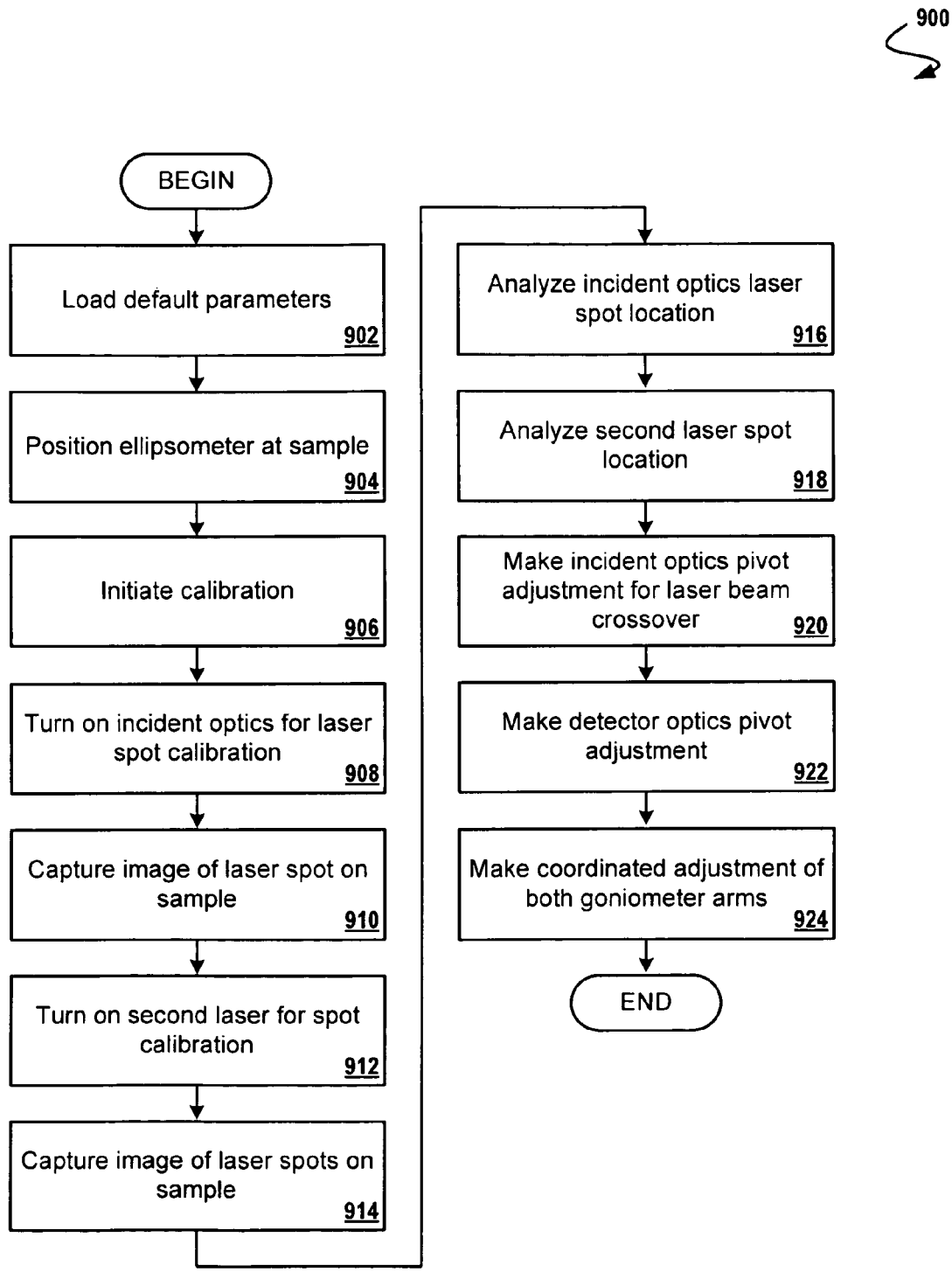
FIG. 9 is a flowchart of steps for calibration of an apparatus for ellipsometric measurements performed on an arbitrarily large sample, using a goniometer design, according to one embodiment.

FIG. 9 is a flowchart of steps for calibration of an apparatus for ellipsometric measurements performed on an arbitrarily large sample, using a goniometer design and two laser sources, according to one embodiment. As an option, the present method 900 may be implemented in the context of the architecture and functionality of FIG. 1 through FIG. 8. As shown, the step 902 begins by loading default parameters. Default parameters might include (but are not limited to) the dimension of the fabric sample, the organization of the samples to be taken over the surface of the fabric, the number of measurements to be taken at a particular spot on the fabric, the start/stop and step size increment values of goniometer adjustments, initial values of the pivot angles, initial values of the goniometer arm angles, etc. In step 904, the ellipsometer system is positioned in relative proximity to the sample. One such configuration is shown in FIG. 1 where the PPME ellipsometer system is mounted within a housing 150. In such a configuration the PPME ellipsometer system might be mounted on wheels, or on a jig so as to provide convenience for completing step 904. Step 906 is for initiating system-to-sample calibration. In some embodiments, calibration is initiated when an operator selects a calibrate function on a user-interface (e.g. computer display, keyboard, mouse, etc), or in some embodiments, calibration begins autonomously when the camera 570 detects a beam crossing within the viewport. The method 900 continues by illuminating a laser spot on the sample using the incident optics (see operation 908), and focusing on that image through the viewport (operation 910). Similarly, method 900 continues by illuminating a second laser spot on the sample using a second laser (see operation 912), and focusing on an image of the two laser spots through the viewport (operation 914).

At this point in the method, the beam crossing can be analyzed. In some embodiments the beam crossing can be done visually using a human operator, whereas in other embodiments, computer vision techniques can be used to calculate the centering adjustment distance $d_{adj}$ of the incident optics laser spot (see operations 916 and 918). In the embodiment of FIG. 9, the values for $d_{adj}$ are translated into adjustments values for pivot point 614 and into goniometer arm adjustments for the incident optics goniometer arm, and into pivot adjustments pivot points 664 and goniometer adjustments for the detector optics goniometer arm (see operations 920, 922, 924).

It should be emphasized that various embodiments may employ any mix of pivot adjustments, and/or both goniometer adjustments, and/or system-to-sample distance adjustments.

In some cases, only pivot adjustments are made during the calibration process; in some cases, only goniometer adjustments adjustment are made (see operations 920 and 922); and in some cases only the coordinated adjustments of both goniometer arms are performed (see operation 924). Other embodiments involve combinations of pivot point adjustments, goniometer adjustments, and even system-to-sample distance adjustments. Of course, repeated goniometer adjustments might be made after various calibration adjustments have been made, for example taking multiple ellipsometric measurements at a single point, and/or varying the angle of incidence for each successive measurement (see operation 924). In other embodiments involving both goniometer adjustments and system-to-sample distance, goniometer adjustments might be made only after the system-to-sample distance adjustments have been made.

In slightly more formal terms, one embodiment of a method for calibrating an apparatus for ellipsometric measurements performed on an arbitrarily large sample, using a visible sample reference frame, can be described as projecting a first laser beam spot from an incident laser source onto a sample, said first laser beam spot location being within the sample reference frame; analyzing the position of said first laser beam spot relative to the center of the sample reference frame; and adjusting an initial physical location using at least one of a plurality of physical elements comprising the apparatus for ellipsometric measurements to achieve a first beam spot location being located about the vertical center of the sample reference frame. As may be now be apparent, the reference frame may be provided by a camera that is mounted with the lens center at the same height (Y-axis direction) as the incident laser beam, and with the vector normal to the focal plane being perpendicular to the sample. The aforementioned is but one technique for calibrating an incident laser source to a centerpoint. Another method involves projecting a second laser beam spot onto a sample, said second laser beam spot location being centered about the Y-axis within the sample reference frame. In such a case the calibration proceeds by analyzing the position of the first laser beam spot relative to the position of said second laser beam spot, and adjusting the first laser beam to project onto the sample such that the projection is substantially centered (with respect to the Y-axis) over the second laser beam. The detector arm may then be calibrated using beam intensity techniques, or using mechanical angle matching techniques.

Another method involves projecting a third laser beam spot, from the proximity of a laser detector onto a sample, said third laser beam spot location being within the sample reference frame; analyzing the position of said first laser beam spot relative to the center of the third laser beam spot; and adjusting the third laser beam to project onto the sample such that the projection is substantially centered (with respect to the Y-axis) over the projection of the first laser beam.

Of course any or all of the aforementioned analyses and adjustments can be performed under computer control using image processing techniques, computer vision techniques, and any form of computer-based mechanical controls.

Figure 10:
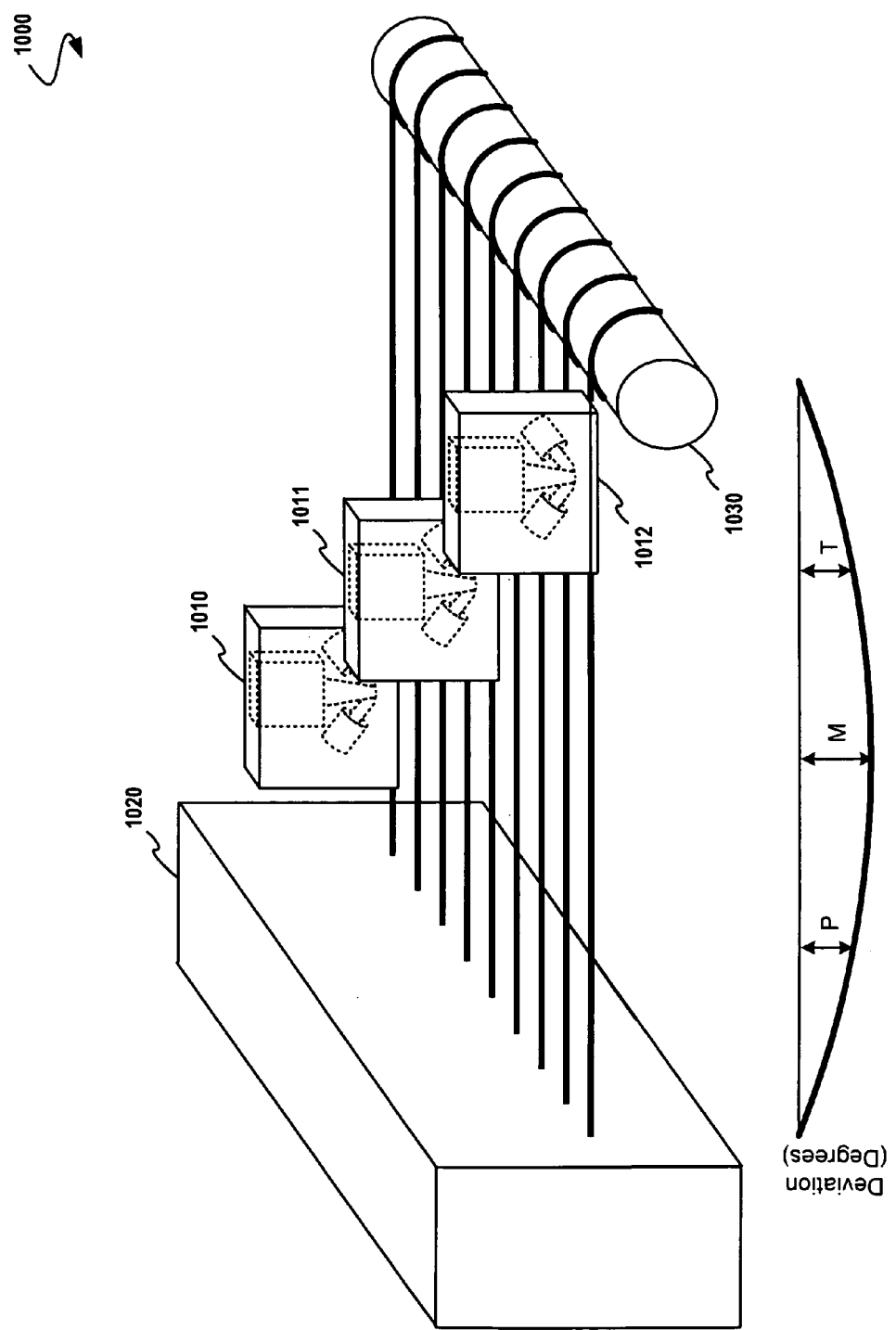
FIG. 10 shows a configuration where a fiber-tow system employs one or more variable wavelength and/or variable incidence angle spectrographic ellipsometers positioned over a fiber-tow system, using a fiber-tow producer and a fiber-tow take-up reel, according to one embodiment.
Figure 11:
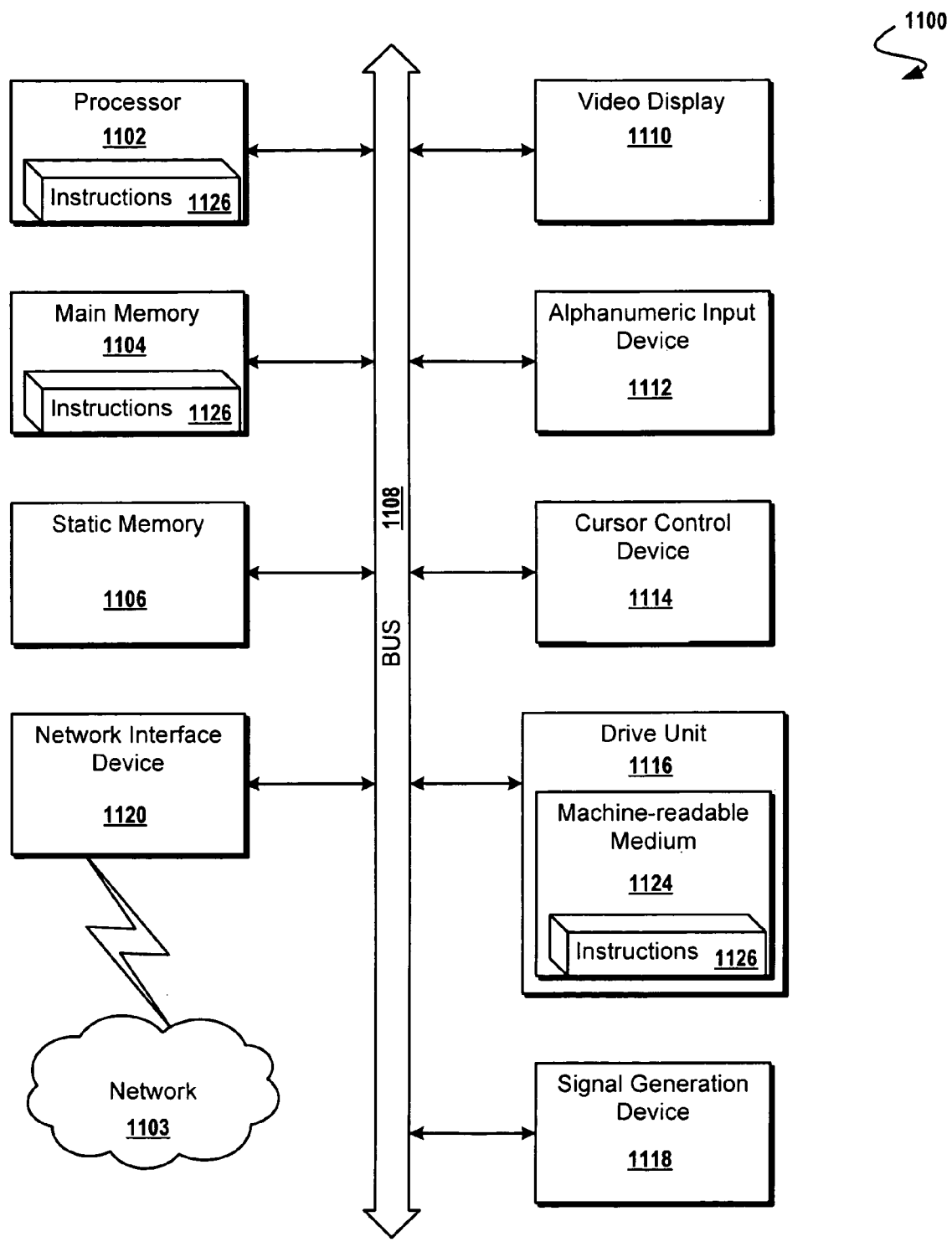
FIG. 11 is a diagrammatic representation of a machine in the exemplary form of a computer system, within which a set of instructions for causing the machine to perform any one of the methodologies discussed herein may be executed, according to one embodiment.

FIG. 10 shows a configuration where a fiber-tow system 1000 employs one or more PPME ellipsometers 1010, 1011, 1012, positioned over a fiber-tow system, using a fiber-tow producer 1020 and a fiber-tow take-up reel 1030, according to one embodiment. As an option, the present system 1000 of FIG. 10 may be implemented in the context of the architecture and functionality of FIG. 1 through FIG. 9. In this environment, the system-to-sample distance adjustments may be controlled by an initial set-up, and so long as the tension and fiber tensile characteristics are constant, the sag remains constant, and as such the system-to-sample distance remains constant for a given PPME ellipsometer (1010, 1011, 1012) located at a particular location along the fiber tow. Of course the sag is substantially a function of gravity, and can be modeled quite accurately, given uniformity of the fiber. The maximum sag is normally found at a midpoint between the fiber producer reel and the fiber tow reel. Any of the aforementioned techniques for adjusting the system-to-sample distance and laser beam crossover point may be used, thus an ellipsometer may be positioned near the fiber producer (e.g. apparatus 1010) or near the fiber tow take-up reel (e.g. apparatus 1012) or anywhere in between (e.g. apparatus 1011). FIG. 11 is a diagrammatic representation of a machine in the exemplary form of a computer system 1100, within which a set of instructions for causing the machine to perform any one of the methodologies discussed above may be executed. The embodiment shown is purely exemplary, and might be implemented in the context of one or more of FIG. 1 through FIG. 10. In alternative embodiments, the machine may comprise a network router, a network switch, a network bridge, a Personal Digital Assistant (PDA), a cellular telephone, a web appliance or any machine capable of executing a sequence of instructions that specify actions to be taken by that machine.

The computer system 1100 includes a processor 1102, a main memory 1104 and a static memory 1106, which communicate with each other via a bus 1108. The computer system 1100 may further include a video display unit 1110 (e.g. a liquid crystal display (LCD) or a cathode ray tube (CRT)). The computer system 1100 also includes an alphanumeric input device 1112 (e.g. a keyboard), a cursor control device 1114 (e.g. a mouse), a disk drive unit 1116, a signal generation device 1118 (e.g. a speaker), and a network interface device 1120.

The disk drive unit 1116 includes a machine-readable medium 1124 on which is stored a set of instructions (i.e. software) 1126 embodying any one, or all, of the methodologies described above. The software 1126 is also shown to reside, completely or at least partially, within the main memory 1104 and/or within the processor 1102. The software 1126 may further be transmitted or received via the network interface device 1120 over the network 130.

It is to be understood that embodiments of this invention may be used as, or to support, software programs executed upon some form of processing core (such as the CPU of a computer) or otherwise implemented or realized upon or within a machine or computer readable medium. A machine readable medium includes any mechanism for storing or transmitting information in a form readable by a machine (e.g. a computer). For example, a machine readable medium includes read-only memory (ROM); random access memory (RAM); magnetic disk storage media; optical storage media; flash memory devices; electrical, optical, acoustical or other form of propagated signals (e.g. carrier waves, infrared signals, digital signals, etc.); or any other type of media suitable for storing or transmitting information.

While the invention has been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

I claim:

1. A method for taking ellipsometric measurements performed on an arbitrarily large sample, using a sample reference frame, comprising:
   projecting a first laser beam spot, from a first incident laser source onto the sample, the first laser beam spot being within the sample reference frame, the first incident laser source being pivotally mounted to a first movable stage;
   analyzing incident laser light reflected off the sample using a detector, the detector being pivotally mounted to a second movable stage; and
   adjusting the first laser beam spot on the sample by moving the first movable stage, thereby causing movement of the second movable stage;
   wherein moving the first movable stage and moving the second movable stage occur in tandem such that a first radial movement of the first stage through a first arc is equal and opposite to a second radial movement of the second stage through a second arc.

2. The method of claim 1 further comprising:
   projecting a second laser beam spot onto the sample, the second laser beam spot location being positioned within the sample reference frame.

3. The method of claim 1 further comprising:
   projecting a third laser beam spot, the third laser beam spot to calibrate a centerpoint the third laser beam spot location being within the sample reference frame; and
   adjusting a position of the first laser beam spot relative to the centerpoint of the third laser beam spot.

4. The method of claim 3, wherein adjusting the position of the first laser beam spot comprises adjusting the first laser beam spot to be located over the centerpoint.

5. The method of claim 1 wherein the first movable stage is mechanically coupled to a semi-circular track.

6. The method of claim 1 wherein the second movable stage is mechanically coupled to a semi-circular track.

7. The method of claim 5 wherein the first arc is formed along the semi-circular track.

8. The method of claim 7 wherein the second arc is formed along the semi-circular track.

9. The method of claim 1, wherein projecting the first laser beam spot from the first incident laser source comprises projecting from a first goniometer arm.

10. The method of claim 2, wherein projecting the second laser beam spot comprises projecting from a laser source mounted to the detector, the detector mounted to a second goniometer arm.

11. The method of claim 1, further comprising display of a human viewable image showing the first laser beam spot on a computer display.

12. A tangible computer readable medium for storing instructions, which when executed by a computer, causes the computer to take ellipsometric measurements performed on an arbitrarily large sample, using a sample reference frame, the instructions for:
   projecting a first laser beam spot, from a first incident laser source onto the sample, the first laser beam spot being within the sample reference frame, the first incident laser source being pivotally mounted to a first movable stage;
   analyzing incident laser light reflected off the sample using a detector, the detector being pivotally mounted to a second movable stage; and
   adjusting the first laser beam spot on the sample by moving the first movable stage;
   wherein moving the first movable stage and moving the second movable stage occur in tandem such that a first radial movement of the first stage through a first arc is equal and opposite to a second radial movement of the second stage through a second arc.

13. The tangible computer readable medium of claim 12 further comprising:
projecting a second laser beam spot onto the sample, the second laser beam spot location being within the sample reference frame.

14. The tangible computer readable medium of claim 12 further comprising:
projecting a third laser beam spot, the third laser beam spot to calibrate a centerpoint, the third laser beam spot location being within the sample reference frame; and
adjusting a position of the first laser beam spot relative to the centerpoint of the third laser beam spot.

15. The tangible computer readable medium of claim 12, wherein adjusting the first laser beam spot comprises adjusting of the first laser spot to be located over a center of the sample reference frame.

16. An apparatus for taking ellipsometric measurements performed on an arbitrarily large sample, using a sample reference frame, the apparatus comprising:
a first incident laser source to project a first laser beam spot, from the first incident laser source onto the sample, the first laser beam spot being within the sample reference frame, the first incident laser source being pivotally mounted to a first movable stage;
a detector to analyze incident laser light reflected off the sample using the detector, the detector being pivotally mounted to a second movable stage; and
an adjustable pivot point to adjust the first laser beam spot on the sample by moving the first movable stage, thereby causing movement of the second movable stage;
wherein moving the first movable stage and moving the second movable stage occur in tandem such that a first radial movement of the first stage through a first arc is equal and opposite to a second radial movement of the second stage through a second arc.

17. The apparatus of claim 16 further comprising:
a second laser to project a second laser beam spot onto the sample.

18. The apparatus of claim 16 further comprising:
a third laser to project a third laser beam spot, the third laser beam spot to calibrate a centerpoint.

* * * * *

UNITED STATES PATENT AND TRADEMARK OFFICE
CERTIFICATE OF CORRECTION

PATENT NO.           : 8,169,612 B2                                            Page 1 of 1
APPLICATION NO.      : 12/474104
DATED                : May 1, 2012
INVENTOR(S)          : Chao Gao It is certified that error appears in the above-identified patent and that said Letters Patent is hereby corrected as shown below:

In the Specification

Col. 1, Line 12, this patent should contain the following requisite patent rights clause: This invention was made with Government support under N68336-09-C-0130 awarded by the Department of Navy.

Signed and Sealed this
Twenty-ninth Day of July, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,169,612 B2 |
| APPLICATION NO. | : 12/474104 |
| DATED | : May 1, 2012 |
| INVENTOR(S) | : Chao Gao |

Page 1 of 1

It is certified that error appears in the above-identified patent and that said Letters Patent is hereby corrected as shown below:

In the Specification

Col. 1, Line 12, this patent should contain the following requisite patent rights clause: This invention was made with Government support under N68335-09-C-0130 awarded by the Department of Navy.

This certificate supersedes the Certificate of Correction issued July 29, 2014.

Signed and Sealed this
Seventh Day of October, 2014

Michelle K. Lee
*Deputy Director of the United States Patent and Trademark Office*